US011186816B2

(12) United States Patent
Thomas et al.

(10) Patent No.: US 11,186,816 B2
(45) Date of Patent: Nov. 30, 2021

(54) MICROBES AND METHODS FOR PRODUCING THE SAME

(71) Applicant: Bayer CropScience LP, St. Louis, MO (US)

(72) Inventors: Varghese P. Thomas, Davis, CA (US); Benjamin L. Golomb, Sacramento, CA (US); Damian Curtis, Davis, CA (US)

(73) Assignee: Bayer CropScience LP, St. Louis, MO (US)

( * ) Notice: Subject to any disclaimer, the term of this patent is extended or adjusted under 35 U.S.C. 154(b) by 95 days.

(21) Appl. No.: 16/245,132

(22) Filed: Jan. 10, 2019

(65) Prior Publication Data

US 2019/0209636 A1  Jul. 11, 2019

Related U.S. Application Data

(60) Provisional application No. 62/615,816, filed on Jan. 10, 2018.

(51) Int. Cl.
| | |
|---|---|
| *C12N 1/36* | (2006.01) |
| *A61K 36/48* | (2006.01) |
| *A01N 65/20* | (2009.01) |
| *C12N 1/20* | (2006.01) |
| *A01H 3/00* | (2006.01) |
| *A01N 63/22* | (2020.01) |
| *A61K 35/00* | (2006.01) |

(52) U.S. Cl.
CPC ............... *C12N 1/36* (2013.01); *A01H 3/00* (2013.01); *A01N 63/22* (2020.01); *A01N 65/20* (2013.01); *A61K 36/48* (2013.01); *C12N 1/20* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 9,150,851 B2 | 10/2015 | Wigley et al. | |
| 2014/0038296 A1 | 2/2014 | Palsson et al. | |
| 2015/0368637 A1* | 12/2015 | Wigley | A01H 3/00 506/1 |
| 2017/0086402 A1 | 3/2017 | Meadows-Smith et al. | |

FOREIGN PATENT DOCUMENTS

| | | |
|---|---|---|
| WO | 2009126795 A1 | 10/2009 |
| WO | 2014046553 A1 | 3/2014 |
| WO | 2015142185 A1 | 9/2015 |
| WO | 2017/196850 A1 | 11/2017 |

OTHER PUBLICATIONS

Bloemberg, G.V., et al., "Molecular Basis of Plant Growth Promotion and Biocontrol by Rhizobacteria," Current Opinion in Plant Biology, 2001, vol. 4, pp. 343-350.
Egamberdieva, D. et al., "Selection for Root Colonising Bacteria Stimulating Wheat Growth in Saline Soils," Biol. Fertil. Soils, 2009, vol. 45, pp. 563-571.
Gangwar, M., et al., "Isolation and Characterization of Endophytic Bacteria from Endorhizosphere of Sugarcane and Ryegrass," The Internet Journal of Microbiology, 2008, vol. 7, No. 1, pp. 1-7.
Kamilova, F., et al., "Enrichment for Enhanced Competitive Plant Root Tip Colonizers Selects fro a New Class of Biocontrol Bacteria," 2005, vol. 7, No. 11, pp. 1809-1817.
Kuiper, I., et al., "Selection of a Plant-Bacterium Pair as a Novel Tool for Rhizostimulation of Polycyclic Aromatic Hydrocarbon-Degrading Bacteria," MPMI, 2001, vol. 14, No. 10, pp. 1197-1205.
Pliego, C., et al., "Screening for Candidate Bacterial Biocontrol Agents Against Soilborne Fungal Plant Pathogens," Plant Soil, 2011, vol. 340, pp. 505-520.
Pliego, C., et al., "Plant Growth-Promoting Bacteria: Fundamentals and Exploitation," Bacteria in Agrobiology: Crop Ecosystems, D.K. Maheshwari (ed.) 2011, Chapter 11, pp. 295-343.
Shankar, M., et al., "Root Colonization of a Rice Growth Promoting Strain of Enterobacter cloacae," Journal of Basic Microbiology, 2011, vol. 51, pp. 523-530.
Validov., S., et al., "Selection of Bacteria Able to Control *Fusarium oxysporum* f. sp. *radicis-lycopersici* in Stonewool Substrate," Journal of Applied Microbiology, 2007, vol. 102, pp. 461-471.
Arensdorf, J., et al., "Chemostat Approach for the Directed Evolution of Biodesulfurization Gain-of-Function Mutants," Feb. 1, 2002, retrieved from the Internet: URL:https://aem.asm.org/content/aem/68/2/691.full.pdf, [retrieved on Mar. 6, 2019], Applied and Environmental Microbiology, vol. 68, pp. 691-698.
Badri, D.V., et al., "Application of Natural Blends of Phytochemicals Derived from the Root Exudates of *Arabidopsis* to the Soil Reveal that Phenolic-Related Compounds Predominantly Modulate the Soil Microbiome," Journal of Biological Chemistry, vol. 288, No. 7, Jan. 4, 2013, pp. 4502-4512.
Canli, K., et al., "Antimicrobial Activity and Chemical Composition Screening of Epilobium montanum Root," Indian Journal of Pharmaceutical Education and Research, vol. 51, No. 3s, Jul. 25, 2017, pp. s239-s243.
International Search Report and Written Opinion of the International Searching Authority for International Patent Application No. PCT/US2019/013101, dated Mar. 18, 2019, 17 pages.
Badri, D.V., et al., "Regulation and Function of Root Exudates," Plant, Cell and Environment, 2009, vol. 32, No. 6, pp. 666-681.
Bais, H.P., et al., "Root Exudates Modulate Plant-Microbe Interactions in the Rhizosphere," Secondary Metabolites in Soil Ecology, 2008, pp. 241-252.
Chaparro, J.M., et al., "Rhizosphere Microbiome Assemblage is Affected by Plant Development," The ISME Journal, 2014, vol. 8, pp. 790-803.
Gresham, D., et al., "The Functional Basis of Adaptive Evolution in Chemostats," FEMS Microbiology Reviews, 2015, vol. 39, pp. 2-16.

(Continued)

*Primary Examiner* — Michelle F. Paguio Frising
(74) *Attorney, Agent, or Firm* — Michelle L. Samonek

(57) ABSTRACT

The disclosure is generally directed to methods for screening, identifying, and producing microorganisms capable of imparting beneficial properties to plants. In some aspects, improved plant-associated soil microorganisms are generated by experimental evolution using a plant root exudate or root exudate compound.

19 Claims, 11 Drawing Sheets

(56) References Cited

OTHER PUBLICATIONS

Redmond, J.W., et al., "Flavones Induce Expression of Nodulation Genes in Rhizobium," Nature, 1986, vol. 323, pp. 632-635.
Sandberg, T.E., et al., "Evolution of *Escherichia coli* to 42° C and Subsequent Genetic Engineering Reveals Adaptive Mechanisms and Novel Mutations," Mol. Biol. Evol., Jul. 10, 2014, vol. 32, No. 10, pp. 2647-2662.

* cited by examiner

**Measured growth rate (slope) estimate of Strain 2 (*Bacillus* WT) and selected population derivatives grown on soybean root exudate – Set 1**

Soy Root Exudate Assay: Adjusted Growth Estimates (showing 90% confidence intervals)

Measured growth rate (slope) estimate of Strain 2 (*Bacillus* WT) and selected population derivatives grown on soybean root exudate – Set 2

Soy Root Exudate Assay: Adjusted Growth Estimates (showing 90% confidence intervals)

**Measured growth rate (slope) estimate of Strain 2 (*Bacillus* WT) and selected population derivatives grown on soybean root exudate – Set 3**

Soy Root Exudate Assay: Adjusted Growth Estimates (showing 90% confidence intervals)

Measured total root surface area (in cm$^2$) obtained from 2 week old soybean seedlings after seed treatment with *Bacillus* WT 2 (Strain 2) and its population derivatives Measured total root length (in cm) obtained from 2 week old soybean seedlings after seed treatment with *Bacillus* WT 2 (Strain 2) and its population derivatives Measured total fresh shoot weight (g) obtained from 2 week old soybean seedlings after seed treatment with *Bacillus* WT 2 (Strain 2) and its population derivatives Measured total dry shoot weight (g) obtained from 2 week old soybean seedlings after seed treatment with *Bacillus* WT 2 (Strain 2) and its population derivatives

MICROBES AND METHODS FOR PRODUCING THE SAME

CROSS REFERENCE TO RELATED APPLICATIONS

This application claims priority to U.S. Provisional Patent Application No. 62/615,816, filed Jan. 10, 2018, the content of which is incorporated herein by reference in its entirety.

TECHNICAL FIELD

The disclosure is generally directed to microorganisms capable of imparting beneficial properties to plants, and methods for screening, identifying, and producing such microorganisms.

BACKGROUND OF THE DISCLOSURE

Researchers have conducted studies related to experimental evolution using *E. coli* as "test subjects." These evolutionary studies have shown that the bacteria adapt to an identical environment over multiple generations, evolving rapidly as to cell size and mean fitness. These researchers are focused on understanding microevolution and lessons it provides as to evolution, in general. Therefore, they use typical laboratory media for cell growth. In addition, they do not screen the resulting microbes for improved qualities directed to a certain purpose but rather analyze outcomes for differences, in general.

U.S. Pat. No. 9,150,851, discloses methods for selecting a microorganism capable of imparting at least one beneficial phenotypic trait to a plant. The methods comprise a number of steps, including growing plants in a growth medium in the presence of a first set of one or more microorganisms, selecting one or more plants based upon a beneficial plant phenotypic trait selection criteria, acquiring a second set of one or more microorganisms from the plants or the plants and the growth medium containing the plants, and repeating the steps one or more times wherein the second set of one or more microorganisms is used as the first set of microorganisms of any successive repeat, and selecting one or more microorganisms associated with imparting a beneficial phenotypic trait to a plant. Accordingly, these methods are time-consuming since they require, among other things, growing and analyzing plants at each iteration of the process.

BRIEF SUMMARY OF EMBODIMENTS OF THE DISCLOSURE

The disclosure provides methods for screening, identifying, and producing microorganisms capable of imparting beneficial properties to plants using, for example, experimental evolution. The disclosure provides methods that enhance plant-associated soil microorganisms (PASMs), which interact with a given plant in order to improve plant growth or health, or to provide other beneficial phenotypic traits, without genetically modifying the plant itself. Such methods may be broadly applied to various plant species (e.g., including species for which limited genetic information is available) and provide other benefits as described in detail herein. Throughout this disclosure, only when followed by the word "cell," the acronym PASM means "plant-associated soil microbial," rather than "plant-associated soil microorganism."

In some aspects, the methods generally comprise: (a) growing a genetically-uniform population of PASM cells in or on a first medium comprising an aliquot of a root exudate or a root exudate compound produced by a plant of interest; (b) harvesting at least some of the resulting PASM cells and growing the harvested PASM cells in or on a second medium comprising an aliquot of a root exudate or a root exudate compound produced by the plant of interest; (c) repeating step (b) at least one time; and (d) selecting, identifying, and/or producing at least one PASM cell that is different compared to the genetically-uniform population. In some aspects, the selected PASM cell has an improved ability to confer at least one beneficial phenotypic trait to a plant compared to the genetically-uniform population. In some exemplary aspects, the PASM cells may be subjected to a plurality of passages (e.g., 5, 10, 20 or more iterations of step (c)) prior to step (d) as part of a high-throughput automated system, as described herein. The root exudate or a root exudate compound may be varied or consistent throughout methods according to the disclosure (e.g., the concentration and/or combination of root exudate compound(s) may be titrated or otherwise modified in different passages prior to selection). In some aspects, the disclosure provides an improved PASM cell derived from a genetically-uniform population of PASM cells obtained from a plant rhizosphere having: (a) an increased growth rate; (b) an increased cell length and/or cell size; (c) an increased biomass; (d) an increased resistance, tolerance or novel immunity to an antimicrobial compound present in root exudate; (e) improved spore germination (e.g., earlier germination or more complete compared to wild type; i.e., a higher percentage of cells germinate compared to wild type, such as at least about 80% germinated cells, at least about 90%, at least about 95%, at least about 99%, or 100%); (f) improved growth of vegetative cells after germination; (g) any genotype or phenotypic trait that imparts improved colonization of plant roots, compared to the genetically-uniform population of PASM cells; and/or (h) improvement of any other favorable physiological or morphological trait of the PASM cells. Such PASM cells may be generated by growing the genetically-uniform population of PASM cells in a culture comprising a root exudate or one or more compounds derived from a root exudate. As used in this disclosure, the term "antimicrobial" means bacteriocidal, bacteriostatic, fungicidal, and/or fungistatic.

In other aspects, the disclosure provides a method for producing PASM cells, comprising: (a) growing a genetically-uniform population of PASM cells in a chemostat in a medium comprising a root exudate compound produced by a plant of interest; and (b) selecting at least one PASM cell that is different compared to the genetically-uniform population. In one aspect, the root exudate compound is an antimicrobial compound that is antimicrobial with respect to the genetically-uniform population of PASM cells grown in step (a).

In some aspects, the selecting step described in the above paragraphs is followed by producing a fermentation product of the selected at least one PASM cell that is different compared to the genetically-uniform population.

In some aspects, the antimicrobial compound is one or more of the following: (a) a phenol, a benzoxazinone, a flavonoid or isoflavonoid, a tannin, a coumarin, a terpenoid, an alkaloid, a t-cinnamic acid, a ferulic acid, a p-coumaric acid, a vanillic acid, a syringic acid, a 4-hydroxyphenylacetic acid, an indoleacetic acid, a benzoic acid, or a rosmarinic acid; (b) a plant-derived monosaccharide, amino acid, peptide, protein, carbohydrate, sugar alcohol or organic acid; and/or (c) a natural or synthetic derivative of any of the compounds or classes of compounds listed in (a) or (b).

In a certain aspect, the one or more antimicrobial compound is an isoflavonoid selected from the group consisting of coumestrol, genistein, glycitein and daidzein. In another aspect, the at least one PASM cell is selected on the basis of increased tolerance to the isoflavonoid. In some aspects, the disclosed method further comprises sampling the PASM cells from an outflow of the chemostat to monitor genetic and/or phenotypic changes in the PASM cells. In other aspects, the concentration of the root exudate compound in the medium is increased during the growth of the PASM cells to increase selective pressure.

In some aspects, the disclosure provides methods for conferring a beneficial phenotypic trait to a plant, comprising applying improved PASM cells produced according to any exemplary aspect described herein to a plant in an amount sufficient to result in stable or transient colonization of the plant. In some exemplary aspects, the improved PASM cells may alternatively be applied to soil or a plant growth medium which is then used to grow a plant of interest.

In an alternative embodiment of the invention, the population of PASM cells in step (a), described above, is not genetically uniform, but is a population of mutant PASM cells derived from one or more parent strains, where such population may or may not include the parent strain. In another aspect of this embodiment, the population of PASM cells in step (a) comprises a collection or consortia of PASM cells from different genera and/or species and/or their mutants.

In another embodiment, the population of PASM cells in step (a) is grown in the presence of a compound that is present in soil and is known to inhibit growth of PASMs, referred to herein as a soil inhibitor. Soil inhibitors encompass root exudate compounds that are produced by plants as well as compounds produced by soil-dwelling predators of PASMs, such as microbes or nematodes, or compounds produced by PASMs that are antimicrobial to the PASM of interest. Thus, not all soil inhibitors are plant-derived.

In one aspect, the methods generally comprise: (a) growing a population, consortia or collection of PASM cells in or on a first medium comprising an aliquot of a soil inhibitor; (b) harvesting at least some of the resulting PASM cells and growing the harvested PASM cells in or on a second medium comprising an aliquot of a soil inhibitor; (c) repeating step (b) at least one time; and (d) selecting, identifying, and/or producing at least one PASM cell that is different compared to the starting population, consortia or collection. The soil inhibitor may be varied or consistent throughout methods according to the disclosure (e.g., the concentration and/or combination of soil inhibitor may be titrated or otherwise modified in different passages prior to selection). In some aspects, the selecting step is followed by producing a fermentation product of the selected at least one PASM cell that is different compared to the starting population, consortia, or collection.

These and other aspects of the disclosure will be discussed in more detail below.

DETAILED DESCRIPTION OF VARIOUS EMBODIMENTS

Figure 1:
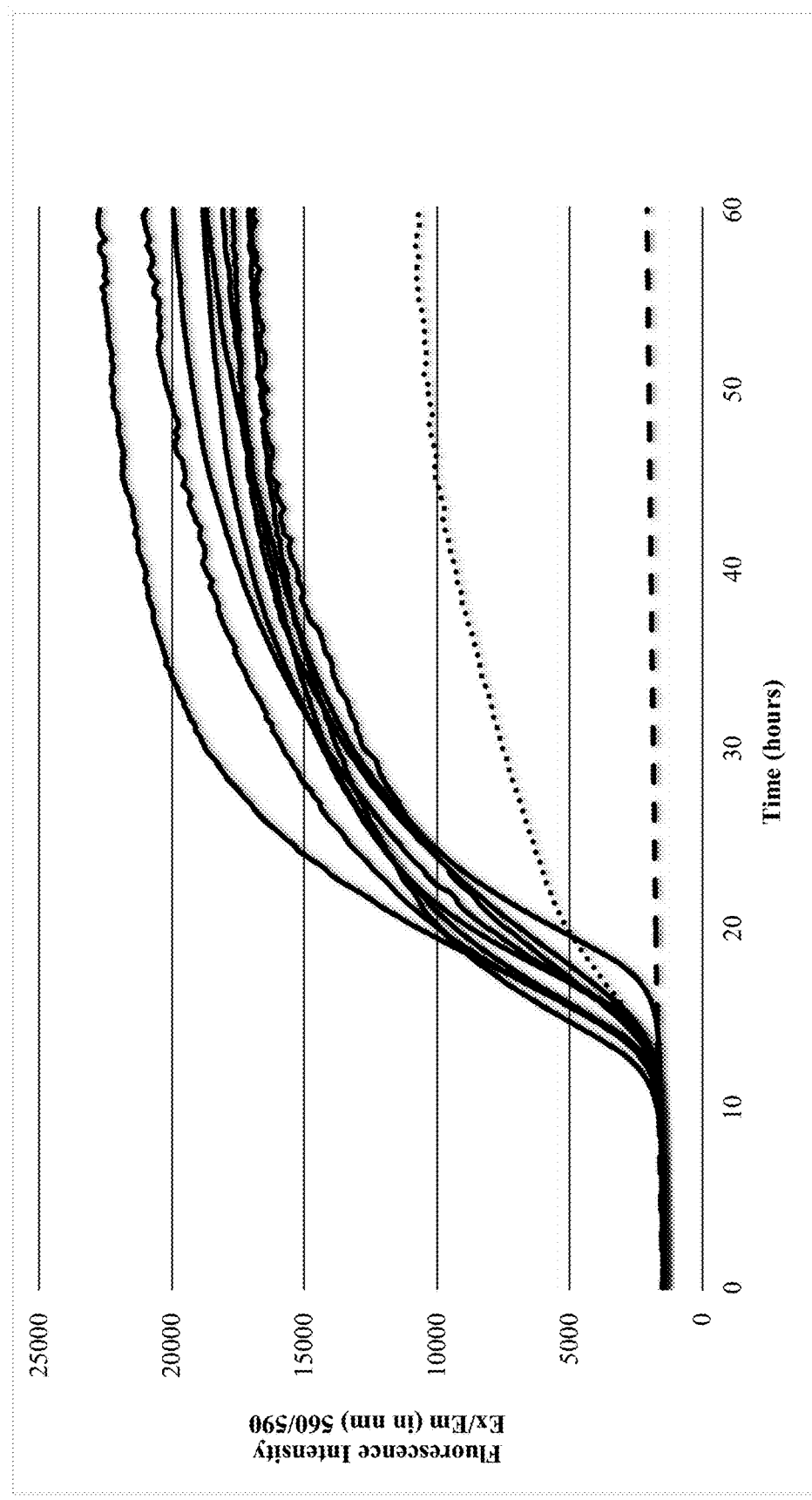
FIG. 1 shows germination start times and growth rates of a wild-type *Bacillus* bacteria (WT) and variants of that bacteria after passaging (A1-A10). WT is the lowest curve shown (other than the flat line, which corresponds to the blank). Viewed from the rightmost point of the graph, the curves for each variant appear in the following order, from highest to lowest: A9, A1, A3, A6, A2, A5, A7, A8, A10.
Figure 2:
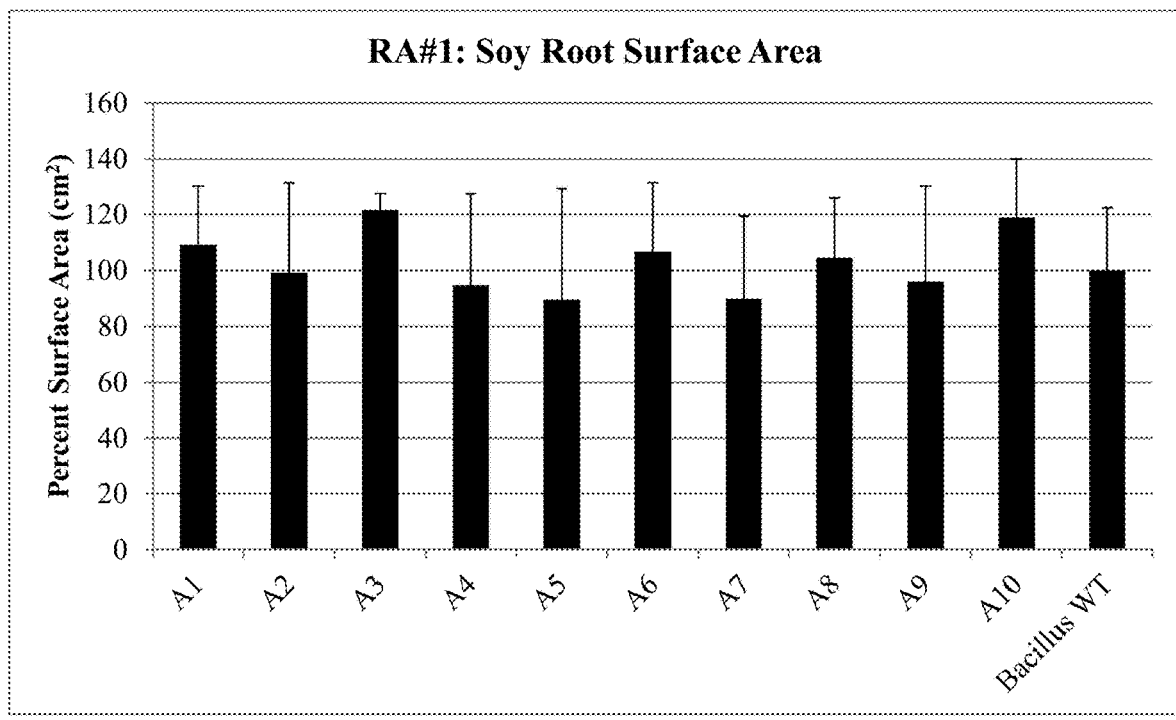
FIG. 2 shows the total percent surface area of soy roots grown from seeds treated with variants of a wild-type *Bacillus* bacteria (A1-A10) compared to roots from seeds treated with the wild-type *Bacillus* bacteria (WT), with the surface area of the roots from the wild-type treated seeds set as 100% surface area.
Figure 3:
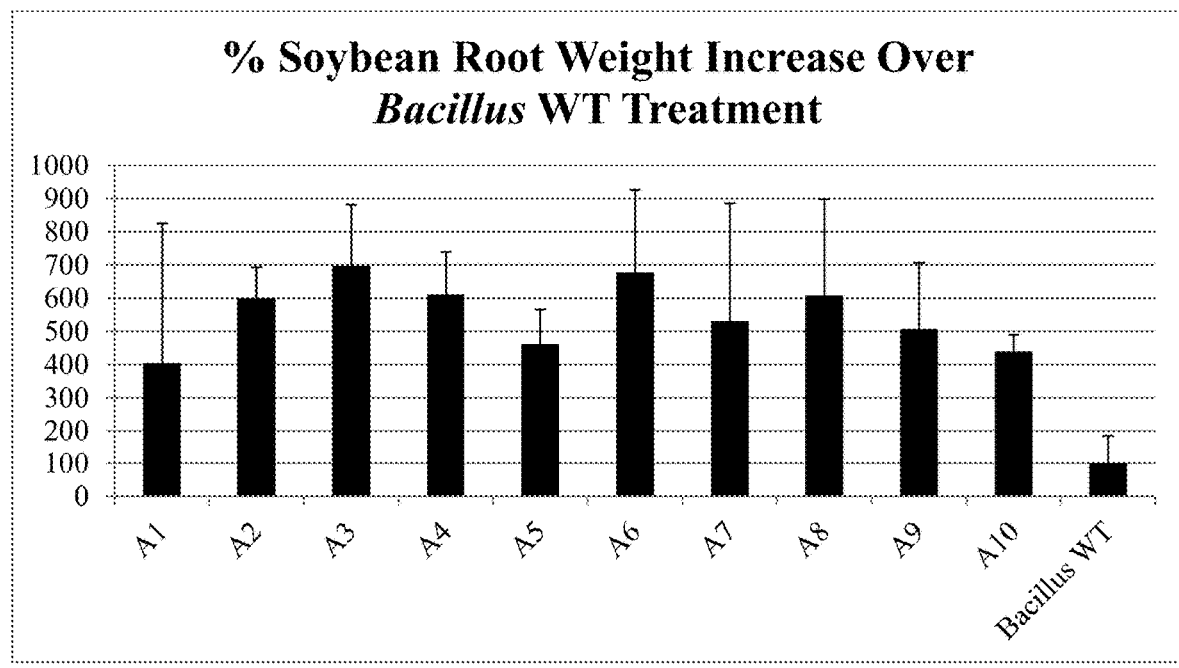
FIG. 3 shows the total percent root weight of soy roots grown from seeds treated with variants of a wild-type *Bacillus* bacteria (A1-A10) compared to roots from seeds treated with the wild-type *Bacillus* bacteria (WT), with the root weight of roots from the wild-type treated seeds set as 100% root weight.
Figure 4:
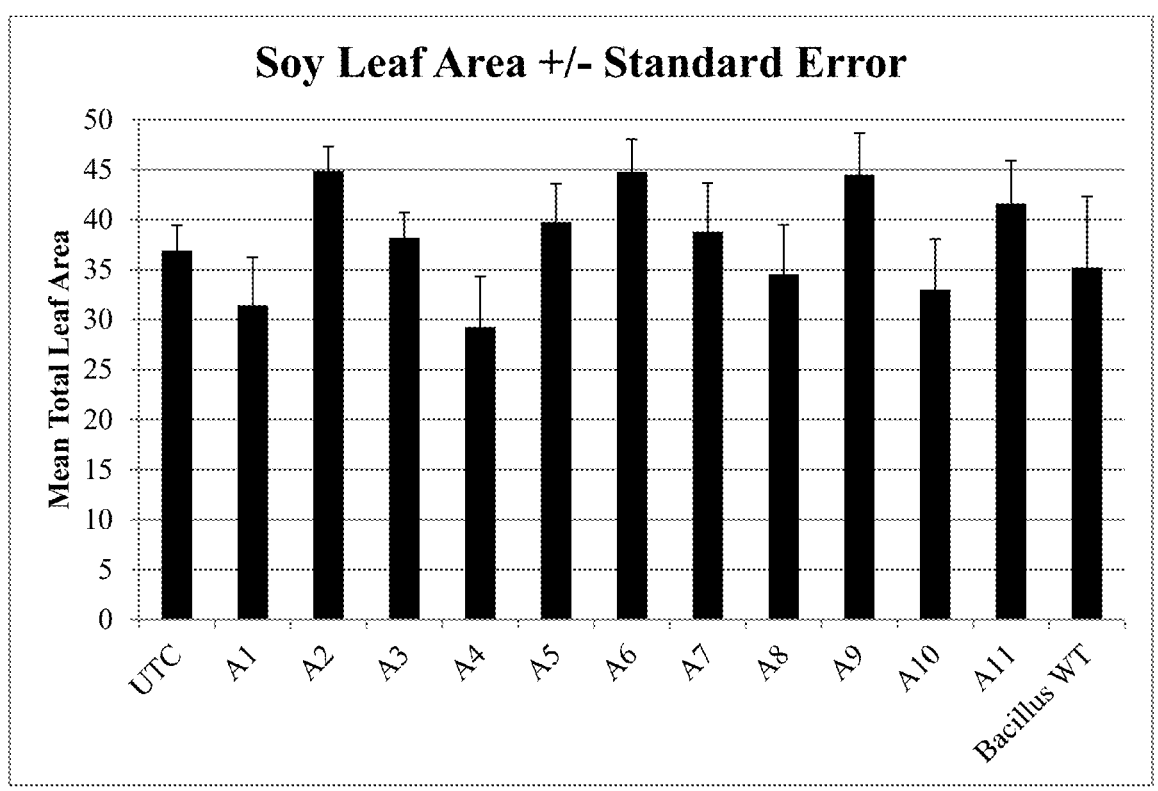
FIG. 4 shows the leaf area of plants grown from seeds treated with the wild-type *Bacillus* bacteria (WT) and variants of that bacteria (A1-A10).

Various methods for screening, identifying, and/or generating PASMs capable of providing beneficial phenotypic traits to plants are described herein. In some exemplary aspects, such methods comprise: (a) growing a population, a collection or a consortia of PASM cells in or on a first medium comprising an aliquot of a soil inhibitor, including a root exudate or a root exudate compound produced by a plant of interest; (b) harvesting at least some of the resulting PASM cells and growing the harvested PASM cells in or on a second medium comprising an aliquot of the soil inhibitor; (c) repeating step (b) at least one time; and (d) selecting at least one PASM cell that is different compared to the starting population, collection or consortia of PASM cells. Compositions comprising improved PASMs and methods of applying the same to plants are also provided.

In some aspects, the present methods use one or more soil inhibitors to drive microbial evolution and co-adaptation to enhance the performance of microbial strains. Soil inhibitors include compounds present in the soil that inhibit growth of one or more PASMs. Soil inhibitors may be plant-derived, such as root exudate, microbially derived, nematode-derived, or added via external sources, such as fertilizers, nitrogen, or other chemical inputs, including pesticides. Examples of soil inhibitors include 2,4-diacetylphloroglucinol (DAPG), pyrrolnitrin, hydrogen cyanide, pyoluteorin, and the root exudate compounds described below.

In some aspects, the present methods use root exudate (or one or more compounds derived from root exudate) to drive microbial evolution and co-adaptation to enhance the performance of microbial strains for improving plants (e.g., enhancing plant health). Without wishing to be bound by any theory, this approach is targeted at improving rhizosphere competency of a microbe (the capacity of a soil microbe to grow and establish on or near by plant roots) by using the crop root exudate. This improved rhizosphere competency leads to microbes better able to improve plant growth and vigor, or which otherwise impart a beneficial phenotypic trait to the plant.

The methods described herein may be performed independent of any observable changes in plant traits and, thus, are amenable to conversion into a high-throughput method using robotics and automation. In particular, the methods may be carried out by passaging, without assessing either the plant or the PASM for improvement between passages, which allows for high-throughput experimental evolution not possible using traditional selection methods, which typically require, among other things, growing and analyzing plants at each iteration of the process.

The plant rhizosphere microbiota comprises numerous PASMs (e.g., bacteria, fungi, protists) that live in the narrow zone of soil that is influenced by the plant's root exudate (secretions). Plant roots secrete a vast array of compounds into the rhizosphere as root exudates, which are a major determinant of microbial community structure in the rhizosphere. In addition, nearly 5% to 21% of all photosynthetically-fixed carbon is transferred to the rhizosphere through root exudates. As described in further detail below, root exudate includes water and water-soluble compounds such as amino acids, organic acids, carbohydrates, sugars, mucilage, vitamins and proteins.

Root exudate modifies the physical and biochemical properties of the rhizosphere and contributes to root growth and plant survival. For example, a root may secrete water to moisten the rhizosphere and enable root expansion or hydroxyl ions to adjust the local pH level and improve the absorption of nutrients. Plants may modify the amount and types of compounds secreted in root exudate in response to physical or biochemical stimuli or to respond to PASMs. For example, compounds may be secreted to specifically reduce the amount of pathogenic bacteria in the local rhizosphere (e.g., antimicrobial compounds) or to encourage the growth of beneficial or symbiotic bacteria (e.g., nutrients and/or signal molecules). As such, the rhizosphere is a dynamic environment and the interactions between a plant and its PASM microbiota play an important role in plant growth, health and the development/expression of significant phenotypic traits.

Root exudation is a key mechanism in the regulation of plant-soil biotic interactions which take place in the rhizosphere. PASMs are known to modulate host physiology to enhance plant functions. In beneficial interactions, soil microbes can influence plant traits including growth, biotic and abiotic stress tolerance and crop yield. The ability of soil-associated microbes to colonize the rhizosphere and achieve microbial establishment requires the capacity to utilize crop root exudates. The chemicals in root exudates act as substrates, chemotactic factors or signaling molecules orchestrating microbial composition and diversity in the crop rhizosphere. See Chaparro et al., "Rhizosphere Microbiome Assemblage is Affected by Plant Development," 2014, *The ISME Journal*, vol. 8, pp. 790-803. The composition of root exudates is influenced by several biotic and abiotic factors including plant age, plant species, environment and microbial colonization of rhizosphere. See Bais et al., "Root Exudates Modulate Plant-Microbe Interactions in the Rhizosphere," 2008, *Secondary Metabolites in Soil Ecology*, pp. 241-252, Springer, Berlin; Badri et al., "Regulation and Function of Root Exudates," 2009, *Plant, Cell and Environment*, vol. 32, no. 6, pp. 666-681. Secondary metabolites in root exudates are also critical in facilitating specialized associations between a plant host and microbe such as *Rhizobium* spp. and legume symbiotic association. See Redmond et al., "Flavones Induce Expression of Nodulation Genes in *Rhizobium*," 1986, *Nature*, vol. 323, pp. 632-635. The contents of each of the above-identified publications, and all subsequent publications cited herein, are incorporated by reference in their entirety as if fully set forth herein.

In nature, the rhizosphere microbiota of a given plant comprises a complex mixture of beneficial, pathogenic and harmless commensal PASMs. As a result, it is difficult to characterize or measure the impact of individual naturally-occurring PASMs on plant growth, health or specific phenotypic traits. Moreover, many effects and phenotypic traits may result as the net effect of multiple PASMs or due to specific interactions between a plurality of PASMs, further complicating efforts to identify specific PASMs which may be useful for agricultural applications. Efforts to identify PASMs with broad applications in agriculture are limited to some extent by the fact that beneficial PASMs may be specific to a given species (or other taxonomic group) of plants. For example, a bacterium that improves the nutrient-uptake, growth rate or other positive phenotypic traits of a first plant species may be unable to colonize the rhizosphere of a second plant species due to antimicrobial compounds present in the root exudate of the second species. Similarly, beneficial PASMs may have evolved to depend on compounds present in the root exudate of a first plant (e.g., as part of a symbiotic relationship), potentially limiting the use of such PASMs with other agriculturally-significant relevant plant species.

The disclosure provides methods that use, for example, experimental evolution to artificially select for and engineer PASMs with specific traits. In some aspects, experimental evolution may be performed by growing a PASM in or on a medium comprising a plant root exudate or at least one root exudate compound, in an iterative fashion, to generate artificially-evolved PASMs with a novel or increased resistance to antimicrobial compounds present in a root exudate. Such methods may be used as a broad platform to direct evolution of improved PASMs with an enhanced resistance or immunity to any arbitrary compound or complex mixture of compounds produced by a plant (e.g., root exudate, diluted or fractionated root exudate, one or more root exudate compounds, etc.) Improved PASMs engineered using these methods may be able to colonize and impart beneficial phenotypic traits to more plant species than the original naturally occurring PASM, allowing for more widespread use of beneficial PASMs in agricultural applications.

Methods for Screening, Identifying and Generating Improved PASMs

In one aspect, the methods described herein use one or more crop root exudates or any component of the root exudate. For example, if it is determined that one component of the root exudate is driving microbe evolution, the current methods may be practiced using a media containing this key component rather than the complete root exudate. The root exudate may be from any plant, such as soybean or corn, or may be a combination of root exudates from multiple plants, such as soybean and corn. Such combinations may drive evolution toward enhanced microbial growth with more than one plant root exudate. The root exudate or a media containing a key component of the root exudate may be used as a medium for growing populations, collections or consortia of PASMs, including genetically uniform populations of one PASM.

The PASM or population, collection or consortia of PASMs can be any microorganism or microorganisms associated with a plant, such as an endospore-forming bacteria (e.g., *Bacillus* species) or gram negative bacteria (e.g., *Bradyrhizobium* species). The PASMs used as a starting point in the methods described herein for directed evolution may be (i) a genetically-uniform population of PASM cells, (ii) a population of PASM cells, which includes a parent strain and its mutants, or mutants derived from a parent strain, or (iii) a collection or consortium of bacterial strains having the same or different genera and/or species. The term "mutant" refers to a genetic variant derived from a parent strain. In one embodiment, the mutant has one or more or all the identifying (functional) characteristics of the parent strain. Such mutants may be genetic variants having a genomic sequence that has greater than about 85%, greater than about 90%, greater than about 95%, greater than about 98%, or greater than about 99% sequence identity to the parent strain(s). Mutants may be obtained by treating cells of the parent strain with chemicals or irradiation or by selecting spontaneous mutants from a population of such parent strain (such as phage resistant or antibiotic resistant mutants), by genome shuffling, or by other means well known to those practiced in the art.

Methods of preparing crop root exudates and growing microorganisms in media are known in the art and exemplified herein. The microorganisms are typically grown to log phase before being transferred; however, this is not a strict requirement.

Root exudate compounds suitable for use with the described methods broadly include, without limitation, any compound present in an exudate of a plant of interest (e.g., carbohydrates, amino acids, enzymes, proteins, peptides, organic acids, sugars, lipids, primary and secondary metabolites, ions, mucilage, and plant hormones such as indole acetic acid). It is understood that such compounds may be antimicrobial or may encourage growth and/or colonization of beneficial, mutualistic, symbiotic or commensal microorganisms. Such compounds may also be signaling compounds (e.g., which regulate, encourage or disrupt chemotaxis) or phytohormones. It is understood that any given root exudate compound may be subject to multiple structural or functional classifications.

Exemplary antimicrobial root exudate compounds include, without limitation: defensive proteins, phytoalexins, indole, benzoxazinone, terpenoids, flavonoids, alkaloids, phenolics (e.g., isoflavonoid derivatives, tannins, and coumarins), isoflavonoids (e.g., isoflavones, isoflavonones such as coumestrol, genistein, glycitein, or daidzein, isoflavans, pterocarpans, rotenoids), organic acids (e.g., rosmarinic, malic, t-cinnamic, ferulic, p-coumaric, vanillic, syringic, 4-hydroxyphenylacetic, indoleacetic, citric acid, succinic acid, and benzoic acids), terpenes (e.g., diterpenes, rhizathalene A), glucosinolates, isothiocyanates, thiocyanates, nitriles, defense-related phytohormones (e.g., jasmonic acid, jasmonates, salicylic acid, and abscisic acid), as well as antimicrobial monosaccharides, polysaccharides, peptides, proteins, and glycoproteins, present in the root exudate of a given plant of interest.

In some exemplary aspects, the root exudate compound may be a plant root derived carbon or nitrogen source. Such compounds include without limitation: phytohormones, amino acids, peptides/proteins, carbohydrates, sugar alcohols, and organic acids.

In some exemplary aspects, the root exudate compound may be a signaling molecule. Exemplary signaling molecules include, without limitation: amino acids (glutamine, arginine, cysteine, asparagine, aspartic acid, cysteine), enzymes, peptides, sugars (oligosaccharides, fructose, arabinose, glucose, mannose, maltose), vitamins, nucleotides, organic acids (ascorbic acid, acetic acid, benzoic acid, ferulic acid, malic acid, citric acid, succinic acid), fungal stimulators, plant inhibitors, chemoattractants (e.g., arabinogalactan proteins), growth regulators, sterols (campestrol, cholesterol, sitosterol, stigmasterol), fatty acids (palmitic, stearic, linoleic, linolenic, oleic), tannins, and phenolic compounds.

The root exudate compounds described herein may be used alone or in combination. For example, a PASM selected from a uniform population may be grown in or on a growth medium comprising any one or a plurality of the root exudates compounds described herein. In some aspects, the presence, amount or concentration of the one or more root exudates compounds may vary between passages (e.g., the concentration of a given root exudate compound may be gradually titrated upward after multiple serial passages). An improved PASM generated using the present methods may be subjected to multiple rounds of passaging using different root exudate compounds (e.g., to generate an improved PASM with increased or novel resistance to multiple antimicrobial root exudate compounds).

Methods according to the disclosure may involve one or more passages of the PASM cells. In some aspects, such methods involve multiple passages prior to selection of an improved PASM cell. Specifically, methods may comprise: (a) growing a genetically uniform population of a PASM in a first aliquot of a root exudate or root exudate compound of a plant of interest; (b) harvesting the resulting PASM cells and growing the harvested PASM cells in a second aliquot of the root exudate or root exudate compound of a plant of interest; and (c) repeating step (b) at least one time. In some aspects, step (b) may be repeated 5, 6, 7, 8, 9, 10, 15, 20, 25, 30, 40, 50, 60, 70, 80, 90, 100 or more than 100 times. Serial passaging may be performed in liquid microbial growth medium supplemented with plant root exudate compound(s). Alternatively, serial passaging may also be performed on solid (e.g., agar) microbial growth medium supplemented with the plant root exudate compound(s). Serial passaging can also be performed on complete plant root exudate, or any arbitrary fraction thereof, both in liquid form or in solid (e.g., agar) form. Artificially-evolved microbial cells produced by the present methods may be selected on the basis of a novel or improved ability to successfully colonize and grow on plant roots and/or in the immediate vicinity of plant roots (i.e., in the rhizosphere of a plant of interest) as compared to the genetically uniform population of microbial cells. In some aspects, improved colonization may result in improved plant health/vigor or may confer a beneficial phenotypic trait to the plant.

It is appreciated that improved PASMs may be obtained after one or more passages. For example, a method according to the disclosure may involve obtaining improved PASMs after every 5 passages. PASMs may be selected based on various characteristics compared to the genetically uniform population, including but not limited to enhanced growth rate, increased biomass, increased cell length and size, and/or, in the case of spore-forming PASMs, earlier germination. Further, PASMs may be selected based on enhanced ability to form a biofilm or general, improved competitive advantage in the rhizosphere, both of which lead to a novel or improved ability to colonize and grow on plant roots and/or in the immediate vicinity of plant roots. Enhanced biofilm formation may be measured and improved PASMs selected by growing the PASMs in soil or a surrogate growing mix and measuring production of compounds known to be present in biofilm, such as extracellular polymeric substances and/or carbohydrate-binding proteins.

Experimental-evolution methods according to the disclosure may be carried out using any of the protocols or parameters described in Sandberg et al., "Evolution of *Escherichia coli* to 42° C. and Subsequent Genetic Engineering Reveals Adaptive Mechanisms and Novel Mutations," *Molecular Biology and Evolution*, 31.10 (2014): 2647-2662, the contents of which is incorporated herein by reference in its entirety. In particular, in some aspects the experimental evolution may be carried out by an automated system as described in the materials and methods section of Sandberg et al. Such automated methods may be configured to allow for passage of batch cultures in mid-exponential phase multiple times a day, enabling many generations of growth in a relatively short time, expediting the selection process. An automated system may be used to control or perform any or all steps of the methods described herein. For example, an automated system may be configured to perform the growth, harvest, and/or selection of PASM cells. In some aspects, these steps may be performed in parallel as part of a high-throughput screening and selection process.

Alternatively, experimental evolution methods may be carried out using any of the protocols or parameters described or cited in Gresham et al., "The Functional Basis of Adaptive Evolution in Chemostats," *FEMS Microbiology Reviews*, 39 (2015): 2-16, the contents of which is incorporated herein by reference in its entirety. In particular, in some aspects the experimental evolution may be carried out in a chemostat, which allows for continuous growth of PASM cells in a constant environment as described in Gresham et al. Chemostats may be configured to allow maintenance of PASM cells in a particular growth phase, such as exponential phase. Chemostats may also be configured such that the root exudate compound is increased gradually as experimental evolution progresses.

In certain aspects, selection, such as selection for tolerance to a root exudate compound, may be accomplished using chemostat selection. Chemostat selection uses a chemostat that allows for a continuous culture of microorganisms wherein the specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source. By altering the conditions as a culture is grown (e.g., increasing the concentration of a root exudate compound), microorganisms in the population that are capable of growing faster at the altered conditions will be selected and will outgrow microorganisms that do not function as well under the new conditions. Typically such selection requires the progressive increase or decrease of at least one culture component over the course of growth of the chemostat culture.

In some aspects, the improved or novel phenotype used to select a variant PASM may include one or more of the following traits: improved growth rate, improved ability to tolerate toxic/growth inhibitory compounds, improved ability to metabolize a component derived from a plant root exudate, or any trait that imparts improved colonization of plant roots.

In certain aspects, the variant PASMs are capable of imparting a phenotypic trait of interest to a plant, such as improved plant vigor. According to the present invention, "improved plant vigor" means that certain crop characteristics are increased or improved by a measurable or noticeable amount over the same factor of the plant produced under the same conditions, but without the application of the composition of the present invention. Improved plant vigor can be characterized, among others, by following improved properties of the plant: (a) improved vitality of the plant, (b) improved quality of the plant and/or of the plant products, e.g., enhanced protein content, (c) improved visual appearance, (d) delay of senescence, (e) enhanced root growth and/or more developed root system (e.g., determined by the dry mass of the root), (f) enhanced nodulation, in particular rhizobial nodulation, (g) longer panicles, (h) bigger leaf blade, (i) increased chlorophyll content, (j) prolonged photosynthetically active period, (k) increased or improved plant stand density, (l) less plant verse (lodging), (m) increased plant weight, (n) increased plant height, (o) tillering increase, (p) stronger and/or more productive tillers, (q) enhanced photosynthetic activity and/or enhanced pigment content and thus greener leaf color, (r) earlier and/or improved germination, (s) improved and/or more uniform and/or earlier emergence, (t) increased shoot growth, (u) earlier flowering, (v) earlier fruiting, (w) earlier grain maturity, (x) less fertilizers needed, (y) less seeds needed, (z) increased yield, and/or (aa) increased resistance to a disease or pest. According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the disclosure or with the application of a parent bacterial strain. Accordingly, in some aspects the yield may be increased by at least 0.5%, or by at least 1%, or by at least 2%, or by at least 4%, or by at least 5%, or by at least 10% when compared to appropriate controls.

Improved PASMs

PASMs with improved traits (e.g., with a novel or increased resistance/immunity to an antimicrobial root exudate compound) may be generated using any of the methods described herein. Suitable PASMs broadly include any plant-associated prokaryotic (e.g., a bacteria or archaea) or eukaryotic (e.g., fungi or protist) microorganisms found in the rhizosphere of a given plant of interest.

Exemplary PASMs include without limitation Proteobacteria (e.g., *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobium, Sinorhizobium* and *Halomonas*), Firmicutes (e.g., *Bacillus, Paenibacillus, Lactobacillus, Mycoplasma,* and *Acetobacterium*), Actinobacteria (e.g., *Streptomyces, Rhodococcus, Microbacterium,* and *Curtobacterium*), and the fungi Ascomycota (e.g., *Trichoderma, Ampelomyces, Coniothyrium, Paecoelomyces, Peni-*

*cillium, Cladosporium, Hypocrea, Beauveria, Metarhizium, Verticullium, Cordyceps, Pichia*, and *Candida, Basidiomycota* (e.g., *Coprinus, Corticium*, and *Agaricus*) and *Oomycota* (e.g., *Pythium, Mucor*, and *Mortierella*). As indicated above, in some aspects PASM may be an endospore-forming bacterium.

Improved PASMs comprise PASMs selected after at least one passage using any of the methods described herein that display new or improved traits compared to (i) the genetically-uniform population of PASM cells selected for directed evolution, (ii) the population of PASM cells selected for directed evolution, which may include a parent strain and its mutants, or mutants derived from a parent strain through any means, or (iii) a collection or consortium of bacterial strains have the same or different genera and/or species. In some aspects, the improved PASM may display an improved ability to confer at least one beneficial phenotypic trait to a plant compared to the starting population, which may be a genetically-uniform population, collection or consortia. For example, the improved PASM may be adapted to colonize a different species of plant that cannot be colonized by members of the starting population (which may in some aspects be a genetically uniform population), collection or consortium of PASM cells.

Methods for Providing Beneficial Phenotypic Traits to Plants Using Improved PASMs Improved PASMs generated using any of the methods described herein may be applied to a plant of interest (e.g., a soybean or corn plant) to confer at least one beneficial phenotypic trait to a plant. It is understood that improved PASMs generated according to the disclosure may be applied to any arbitrary plant of interest capable of being transiently or stably colonized by the improved PASM, or which would otherwise receive an improved phenotypic trait based on exposure to the PASM.

In some exemplary aspects, the improved PASM may be applied directly to a plant or to soil (or other growth media) prior to or after planting. Compositions comprising one or more improved PASMs according to the present disclosure may be applied in any desired manner, such as in the form of a seed coating, soil drench, and/or directly in-furrow and/or as a foliar spray and applied either pre-emergence, post-emergence or both.

In exemplary aspects, after the selection step, the selected, improved PASM(s), which is different from the starting population, consortia or collection of PASMs, is fermented. The resulting fermentation product may be processed (e.g., through concentration and/or drying) and formulated with a carrier that is suitable to the desired application. Such formulated fermentation product is then applied to a plant or plant part (e.g., to a seed) or to the locus surrounding the plant (e.g., soil), in one of the manners described above. Fermentation and formulation are described further below.

Compositions of the present invention include biologically pure cultures of the selected, improved PASMs described herein. The term "biologically pure culture" refers to a population of cells growing in the absence of other species in a predetermined culture media under controlled laboratory or manufacturing conditions and includes a clonal bacterial population or a genetically uniform population. Conventional large-scale microbial culture processes include submerged fermentation, solid state fermentation, or liquid surface culture. Fermentation is configured to obtain high levels of colony forming units and to promote sporulation, in spore-forming microorganisms, such as *Bacillus* species. The bacterial cells, spores and/or metabolites in culture media resulting from fermentation may be used directly or concentrated by conventional industrial methods, such as centrifugation or filtration such as tangential-flow filtration or depth filtration, and evaporation.

Compositions of the present invention include the products of the microbial culture processes described herein. In embodiments in which submerged fermentation is used as the culture process, the product is referred to as a "fermentation broth." Such broth may be concentrated, as described above. The concentrated fermentation broth may be washed, for example, via a diafiltration process, to remove residual fermentation broth and metabolites. The term "broth concentrate," as used herein, refers to fermentation broth that has been concentrated by conventional industrial methods, as described above, but remains in liquid form. The term "fermentation product," as used herein, refers to fermentation broth, broth concentrate and/or dried fermentation broth or broth concentrate.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers may also be added post-drying.

In one embodiment, the fermentation product comprises at least about $1 \times 10^5$ colony forming units (CFU) of the selected, improved PASM. In another embodiment, the fermentation product comprises at least about $1 \times 10^6$ CFU of the selected, improved PASM. In yet another embodiment, the fermentation product comprises at least about $1 \times 10^7$ CFU of the selected, improved PASM. In another embodiment, the fermentation product comprises at least about $1 \times 10^8$ CFU of the selected, improved PASM. In another embodiment, the fermentation product comprises at least about $1 \times 10^9$ CFU of the selected, improved PASM. In another embodiment, the fermentation product comprises at least about $1 \times 10^{10}$ CFU of the selected, improved PASM. In another embodiment, the fermentation product comprises at least about $1 \times 10^{11}$ CFU of the selected, improved PASM. In one exemplary aspect, the selected, improved PASM is a clonal population of one PASM or a genetically uniform population of one PASM.

The following non-limiting examples are provided to further illustrate the present disclosure.

EXAMPLES

Example 1: Selection of Improved *Bacillus* Spores Using Passaging Techniques Soybean root exudate was used as media for growing ten genetically uniform base populations of spores of a *Bacillus* species. TSB Schaeffer's media was inoculated with a single colony of *Bacillus* species and grown at 30° C. for 4-5 day. Spores were washed and heat treated at 80° C. for 30 minutes. Ten independent selection lines were picked for continuous propagation on root exudate. This *Bacillus* parent strain is referred to throughout Examples 1-3 and the corresponding figures as "wild-type" or "*Bacillus* WT."

To generate soybean root exudate, sterilized soybeans (*Glycine max*) were grown in deep well blocks in 1 mL of water in a growth chamber at 25° C. After 1 week the root exudate was harvested, vacuum filtered and stored at −80° C. Composition of the soybean root exudate generated in this manner (using the same germplasm and growing conditions) was tested and composition of various lots determined to be uniform.

100 µL spores (0.20 OD) were grown in soybean root exudate at 30° C. until log phase. Then, the cells were transferred to a new sample of soybean root exudate and again grown to log phase at 30° C. ($OD_{600}$ was measured periodically and samples taken at 0.3 to 0.6.) This process was repeated 13 times over four weeks. Each repetition is referred to in these Examples as a "passage," and strains resulting from each passage having different morphology than the wild-type are referred to as "variants." Variants were identified after every five or, for the last passages, three passages to confirm differences from the parent population during the passaging process. Ten variants from the last ($13^{th}$) passage were assessed according to the assays described below. The wild-type was selected as the "parent" strain because it performs relatively poorly in soybean root exudate compared to other *Bacillus* strains when speed of spore germination, rate of growth and maximum yield are considered.

The variants collected after the last passage were tested for: (i) ability to sporulate, (ii) cell area and length (morphometrics), and (iii) bacterial cell growth kinetics when grown in soybean root exudate. Without wishing to be bound by any theory, Applicant hypothesizes that enhanced growth is more likely to be observed in the media in which passaging was conducted.

To assess retained ability to sporulate, each variant was grown to sporulation in 250 mL flasks with 50 mL sterile Schaeffer's media. A sterile loop was used to transfer a single colony from a streak plate into the media. Flasks were kept in a shaker set to 220 rpm at 30° C. and incubated for 3-5 days and spores assessed via flow cytometry. All variants maintained the ability to sporulate, although sporulation ability varied among variants.

Cell area and length were analyzed via scanning electron microscope (SEM) imaging. Images were analyzed using ImageJ software, with which five single cells were measured, according to the methods described in Schindelin et al., (2012), "Fiji: An Open-Source Platform for Biological-Image Analysis," *Nat. Methods,* 9(7): 676-682. Differences in cell area when samples were grown in Luria broth are shown in Table 1 below.

TABLE 1

| Variant | Average ($µm^2$) | Standard Deviation |
|---|---|---|
| A1 | 2.2482 | 0.395657 |
| A2 | 3.8928 | 0.253903 |
| A3 | 2.4068 | 0.266138 |
| A4 | 2.5328 | 0.298169 |
| A5 | 2.114 | 0.179901 |
| A6 | 3.488 | 0.409976 |
| A7 | 1.9132 | 0.17174 |
| A8 | 3.9214 | 0.292396 |
| A9 | 2.0084 | 0.236402 |
| A10 | 3.038 | 0.439298 |
| WT | 1.052 | 0.113263 |

Equal amounts of soy root exudate and spore solutions of each variant (OD 0.2) and of wild-type were combined into a 96-well microplate along with Presto Blue cell viability reagent (available from Thermo Fisher Scientific). Plate readers were used to measure fluorescent intensity. Germination rate, germination time, and maximum growth were used to calculate adjusted growth rate estimates. Differences in growth from wildtype are shown in FIG. 1. The variants all show increased ability to grow in soy root exudate as compared to the parent *Bacillus* strain.

Swarming motility of the variants and wild-type was assessed in an assay described in Patrick et al., "Laboratory Strains of *Bacillus subtilis* Do Not Exhibit Swarming Motility," *Journal of Bacteriology* (2009) 191(22): 7129-7133. All of the variants showed decreased ability to swarm and swim when compared to the wild-type.

Example 2: Growth Chamber Assays with Variant Strains

The variants and wild-type were used to treat seeds to determine whether the variants resulted in larger root surface area compared to seeds treated with the wild-type strain. Specifically, the wild-type and variants were grown in TSB Schaeffer at 30° C. for 3-5 days. $1\times10^6$CFU/seed of each strain was used to treat corn and soybean seeds. After seeds were grown in sterile sand for seven days at 28° C., roots were harvested, washed, weighed and analyzed using the WhinRhizo software to determine total root surface area (FIG. 2). Root weight from seed treated with the various strains is shown in FIG. 3. Variants increased root weight compared to the wild-type.

Example 3: Greenhouse Study

Soybean seeds were treated with the variants and wild-type at a rate of $1\times10^6$CFU/seed and grown for three weeks under greenhouse conditions. Total leaf area of resulting plants was then measured. Results are shown in FIG. 4.

Example 4: Experimental Evolution of *Bacillus* Cells on Selected Soy Root Exudate Compounds in Liquid Growth Medium A genetically uniform population of *Bacillus* cells can be evolved to overcome toxicity and/or growth inhibition of selected soy root exudate compounds by serially passaging bacterial cells in standard bacterial growth medium supplemented with selected soy root exudate compounds. Exemplary soy root exudate compounds include isoflavones such as coumestrol, genistein, glycitein and daidzein.

To perform experimental evolution, a single colony of the *Bacillus* strain to be evolved is inoculated into standard bacterial growth medium (e.g., LB Lennox) supplemented with the selected soy root exudate compound at a concentration (typically 2-5 μg/mL for isoflavones) that decreases the specific growth rate relative to uninhibited growth. Optionally, more than one selected soy root exudate compound can be supplemented to evolve the *Bacillus* cells to evolve tolerance to each selected soy root exudate compound simultaneously.

Serial passaging is performed by growing *Bacillus* cells in baffled shake flasks with agitation (220 RPM) at the optimal growth temperature for the strain (30-37° C.) or a non-ambient temperature with the selected soy root exudate compound. Cells are incubated until late exponential phase (determined by optical density) at which point a subculture of the cells is inoculated into a fresh flask. This process is repeated until the desired tolerance to the selected soy root exudate compound is achieved. Optionally, the concentration of the selected soy root exudate compound can be increased at each serial passage as appropriate.

At the conclusion of serial passaging, the evolved population is streaked onto solid bacterial growth medium to isolate individual evolved cells. Colonies arising from individual evolved cells are screened for improved tolerance to the selected soy root exudate compound. To assess tolerance, individual evolved isolates are grown in standard growth medium supplemented with the selected soy root exudate compound and growth rate is measured by optical density. Evolved isolates will have increased growth rates relative the parental strain. Alternatively, evolved populations can be streaked onto solid bacterial growth medium supplemented with the selected soy root exudate compound. Cells with evolved tolerance to the selected soy root exudate compound will form colonies faster than cells without evolved tolerance and can be subsequently selected in this manner.

Example 5: Experimental Evolution of Bacillus Cells on Selected Soy Root Exudate Compounds on Solid Growth Medium A genetically uniform population of Bacillus cells can be evolved to overcome toxicity and/or growth inhibition of selected soy root exudate compounds by serially passaging bacterial cells on solid agar standard bacterial growth medium supplemented with selected soy root exudate compounds. Examples of selected soy root exudate compounds can be isoflavones such as coumestrol, genistein, glycitein and daidzein.

To perform experimental evolution, a single colony of the *Bacillus* strain to be evolved is inoculated into liquid standard bacterial growth medium (e.g., LB Lennox) and incubated for 24 hours using standard growth conditions to prepare a liquid inoculum. The liquid inoculum is then plated onto solid agar bacterial growth medium (LB Lennox agar) supplemented with the selected soy root exudate compound at a concentration (typically 2-5 μg/mL for isoflavones) that decreases the specific growth rate (as determined by colony formation speed) relative to uninhibited growth. Optionally, more than one selected soy root exudate compound can supplemented to evolve the *Bacillus* cells to evolve tolerance to each selected soy root exudate compound simultaneously.

Serial passaging may be performed by growing *Bacillus* cells on solid growth medium at the optimal growth temperature for the strain (e.g., 30-37° C.) or a non-ambient temperature with the selected soy root exudate compound. Cells are incubated until visible colonies are formed. The largest colonies are scraped from the plate and resuspended in buffer (e.g., phosphate buffered saline) and plated onto fresh solid growth medium with the selected soy root exudate compound. This process is repeated until the desired tolerance to the selected soy root exudate compound is achieved. Optionally, the concentration of the selected soy root exudate compound can be increased at each serial passage as appropriate.

At the conclusion of serial passaging, the evolved colonies are streaked onto solid bacterial growth medium to isolate individual evolved cells. Colonies arising from individual evolved cells are screened for improved tolerance to the selected soy root exudate compound. To assess tolerance, individual evolved isolates are grown in standard growth medium supplemented with the selected soy root exudate compound and growth rate is measured by optical density. Evolved isolates will have increased growth rates relative the parental strain.

Example 6: Experimental Evolution of Strains of *Bacillus amyloliquefaciens* and *Bacillus megaterium*

Experimental evolution was conducted on a single colony of a *Bacillus amyloliquefaciens* strain ("Strain 2") and a *Bacillus megaterium* strain ("Strain 3") to obtain strains that were tolerant to isoflavones. Preliminary experiments were performed to determine the concentration of a 1:1 mixture of coumestrol and genistein prepared in dimethyl sulfoxide ("DMSO") needed to inhibit growth of the above-identified strains. Experiments were also conducted to ensure that DMSO did not inhibit growth of either strain.

Seed cultures of seven clonal bacterial populations of Strain 2 and Strain 3 were used to inoculate LB Lennox media (available from US Biological Life Sciences—Catalog No. L1505) supplemented with a stock solution of genistein and coumestrol prepared in DMSO and grown overnight at 30° C. at a stirring speed of 1200 rpm in multi-milliliter vessels on an automated platform. Growth was measured via $OD_{600}$ with a plate reader. The initial concentration of genistein and coumestrol, referred to herein as the inhibitory compounds, in LB Lennox media, was 4 μg/mL each. This concentration is referred to as the "Initial Stressor Concentration [μg/mL]" in Table 2, below.

The cultures were maintained at continuous exponential growth (i.e., log phase) over the course of the experiment. Strain 2 was grown for 40 days and produced about 360 generations per population. Strain 3 was grown for 40 days and produced about 280 generations per population. The concentration of the inhibitory compounds was increased when a growth rate of greater than or equal to 0.35 OD/hr. was observed at each concentration. Population fitness varied with added inhibitory compounds but remained in the range of 0.1-0.4 OD/hour over the course of the experiment.

As shown in Table 2, at the end of the experiment, the tolerance of both strains increased several magnitudes for each population. Replicate populations from the same starting strain all evolved to similar final concentration values of the inhibitory compounds, except for the fourth replicate of Strain 2, which reached a somewhat lower concentration.

TABLE 2

| Strain | Replicate | Generations | Initial Stressor Concentration [μg/mL] | Final Stressor Concentration [μg/mL] | Fold Change |
|---|---|---|---|---|---|
| Strain 2 | 1 | 401.24 | 8 | 110.4 | 13.8 |
| | 2 | 341.24 | | 118.8 | 15.0 |
| | 3 | 337.12 | | 112.8 | 14.1 |
| | 4 | 343.56 | | 69.6 | 8.7 |
| | 5 | 370.80 | | 112.4 | 14.0 |
| | 6 | 366..03 | | 132.8 | 16.6 |
| | 7 | 372.18 | | 122.4 | 15.3 |
| Strain 3 | 1 | 278.70 | 8 | 60.4 | 7.6 |
| | 2 | 280.16 | | 58.8 | 7.4 |
| | 3 | 326.54 | | 55.2 | 6.9 |
| | 4 | 259.98 | | 52.4 | 6.6 |
| | 5 | 257.25 | | 48.8 | 6.1 |
| | 6 | 293.33 | | 50.0 | 6.3 |
| | 7 | 276.47 | | 52.8 | 6.6 |

Example 7: Growth of Derivative Populations from Strain 2 in Soybean Root Exudate Eighty two of the derivative populations of Strain 2 generated during the experimental evolution experiment described in Example 6 at different time points after increase of ability to tolerate the initial stressor concentration and after the growth rate had reached the threshold level of greater than or equal to 0.35/hour were collected and further tested. Continuous rounds of selection created genetic variation within the clonal population with mutations, genetic drift, gene flow, etc. These new populations, which were not genetically uniform, will be referred to in this and the following examples as derivative populations. They were grown in soybean root exudate and growth rate compared to that of Strain 2.

Glycerol stock of each derivative population was streaked onto tryptic soy agar ("TSA") and allowed to incubate overnight at 30° C. On the next day, confluent cells were used to inoculate 50 mL TSB Schaeffer's medium contained in a 250 mL baffled shake flask. The shake flasks were then placed on a shake incubator set at 30° C., 220 RPM for 5 days until sporulation was reached.

To generate soybean root exudate, a sterilized soybean variety was grown in culture test tubes in 1 mL of sterile deionized water in a growth chamber at 25° C. light and then transferred onto a rotating platform for aeration (dark cycle) daily. After 1 week the root exudate was harvested, vacuum filtered and stored at −80° C.

91 µL of spores (~0.20 OD) of Strain 2 and the above-described 82 derivative populations were grown in 91 µL of soybean root exudate in quadruplet randomized replicates in a 96 well plate with 18 µL of Presto Blue cell viability reagent (available from Thermo Fisher Scientific) overlaid to the entire plate. The plate was incubated at 30° C. until stationary phase was reached. Fluorescence was measured every 20 minutes for 60 hours.

Figure 5:
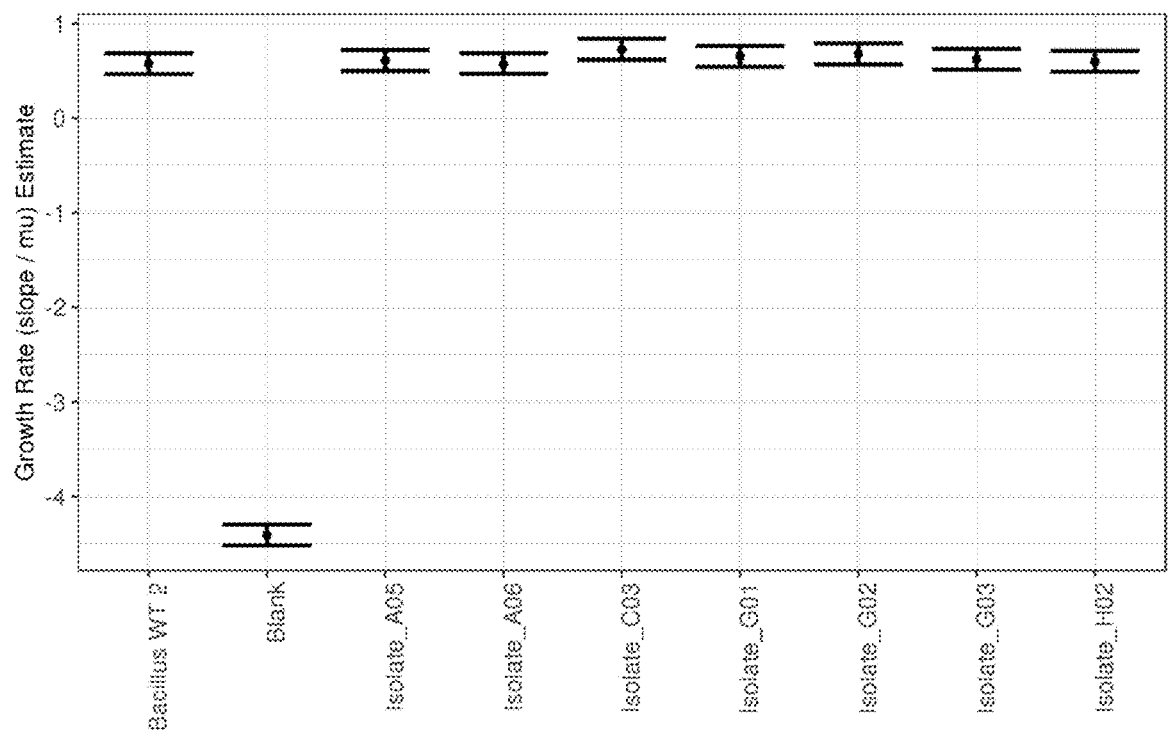
FIG. 5 shows the growth rate of a first set of Strain 2 (referred to in the figure as *Bacillus* WT 2) and selected derivative populations grown on soybean root exudate.
Figure 6:
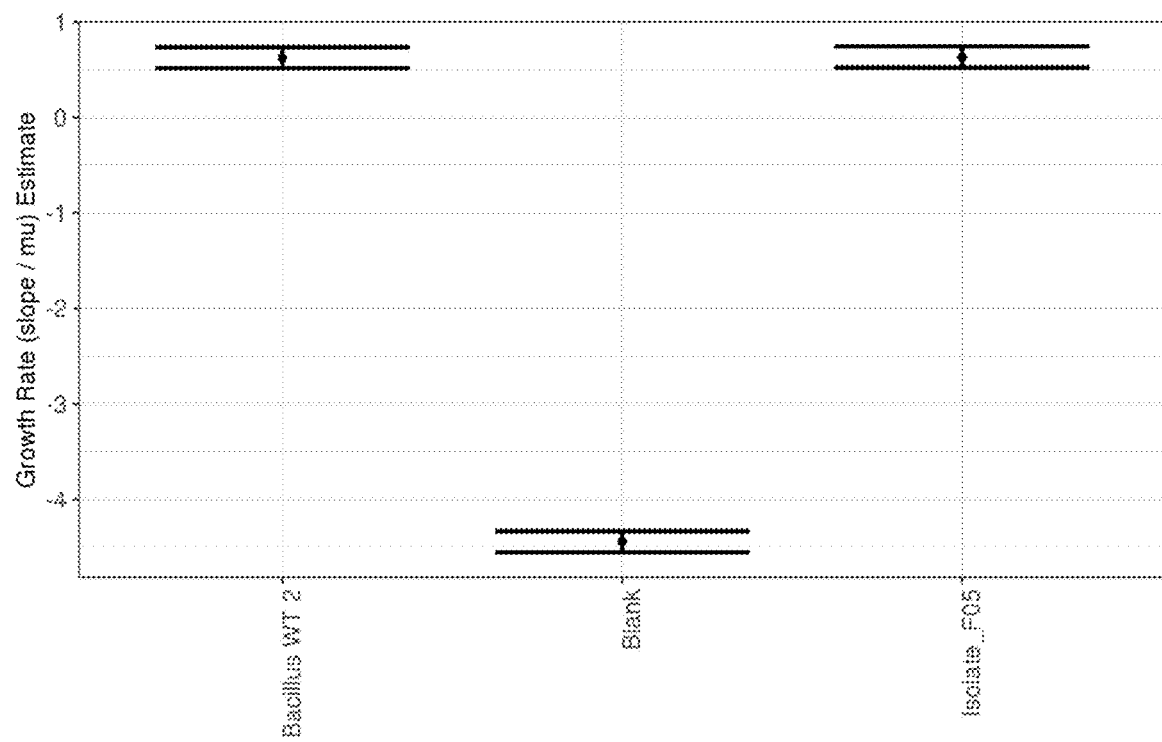
FIG. 6 shows the growth rate of a second set of Strain 2 and selected derivative populations grown on soybean root exudate.
Figure 7:
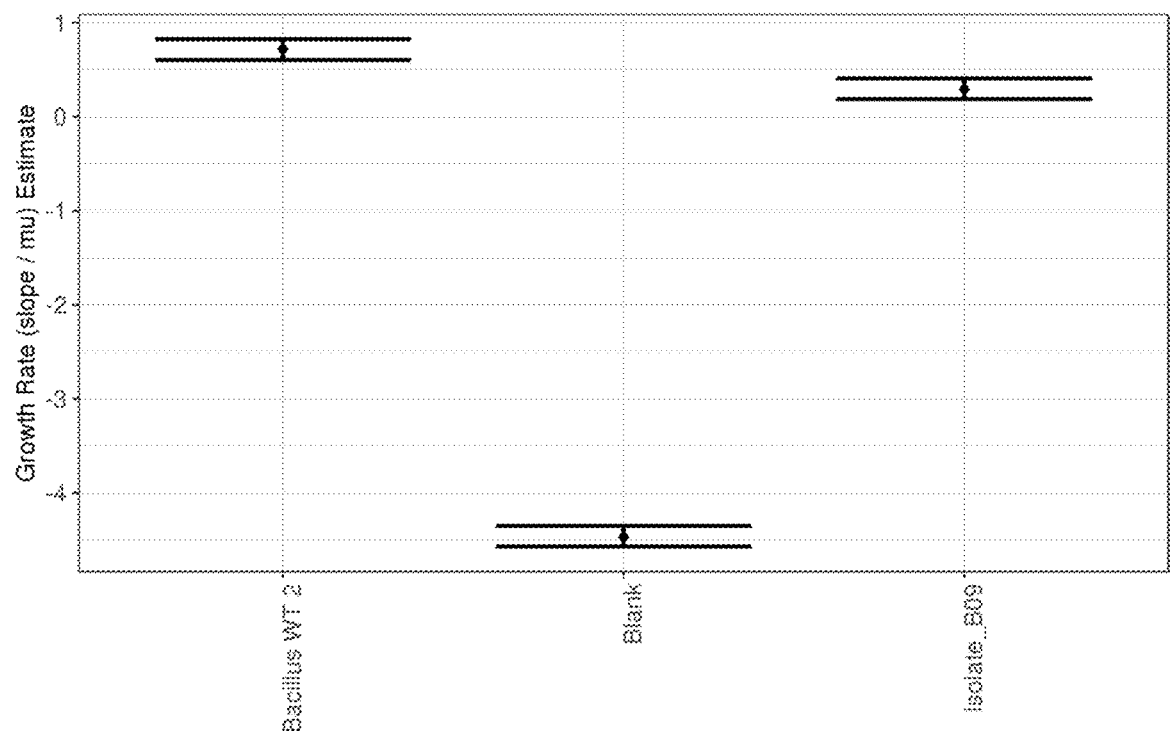
FIG. 7 shows the growth rate of a third set of Strain 2 (referred to in the figure as *Bacillus* WT 2) and selected derivative populations grown on soybean root exudate.

The 82 derivative populations were tested for improvements in spore germination and cell growth kinetics on soybean root exudate in comparison to Strain 2. As expected, the derivative populations did not show improvements compared to Strain 2 during the lag phase of growth, as the concentration of inhibitory compounds was increased during log phase rather than lag phase. See Example 6. Differences in growth rate during log phase were observed between the population derivatives and Strain 2. The 82 population derivatives were tested in four sets with each set compared to Strain 2 and a blank that was included in each run. Strain 2 is referred to as "*Bacillus* WT 2" in the figures. The "blank," or negative control, contained no microbe and was included to check for contamination. FIGS. 5, 6, and 7 show growth estimate, which was the slope of the fluorescence measurements over time during log phase, of Strain 2 and a selection of derivative populations grown in soybean root exudate in three of the four sets. Seven derivative populations from set 1 (FIG. 5), one derivative population from set 2 (FIG. 6) and one derivative population from set 3 (FIG. 7) showed a positive trend of improvement or similar performance in bacterial growth rate estimate to Strain 2 and were selected for further testing in in planta bioassay to measure for any improvement in plant growth promotion, as described in Example 8, below. Data is not shown for the population derivatives that did not show improved bacterial growth rate compared to Strain 2.

Example 8: Greenhouse Assays with Variant Populations

Figure 8:
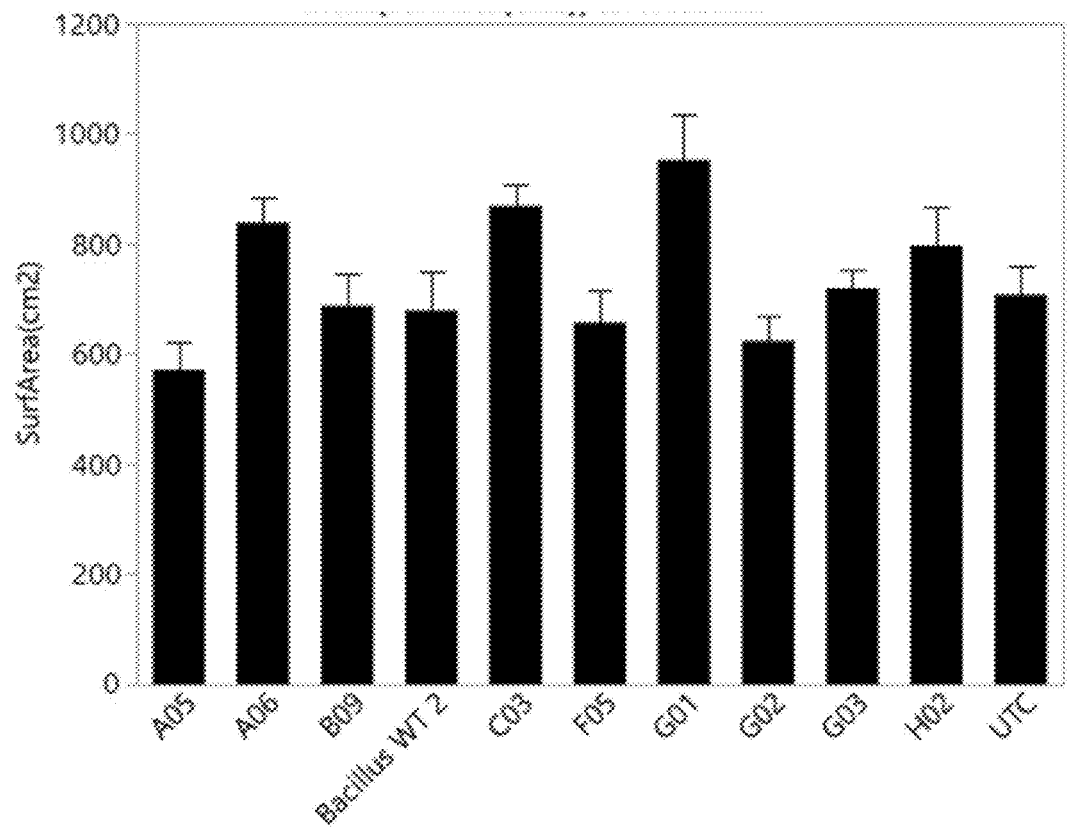
FIG. 8 shows total root surface area (in $cm^2$) of two-week old soybean seedlings treated with Strain 2 (referred to in the figure as *Bacillus* WT 2) and selected derivative populations.

A smaller number of the 82 derivative populations were selected based on demonstrated similar performance or improvement in growth kinetics compared to Strain 2 (as described in Example 7). These derivative populations were further tested in in planta screening to check for improved plant growth promotion on soybean. These derivative populations and Strain 2 (i.e., the wild-type, parent strain) were used to treat seeds to determine whether the variant populations resulted in increased plant biomass compared to seeds treated with the wild-type strain. Specifically, the wild-type and variants were grown in TSB Schaeffer at 30° C. for 3-5 days. $1 \times 10^6$ CFU/seed of Strain 2 or each derivative population was used to treat soybean seeds. After seeds were grown in a mixture of synthetic media and sand for fourteen days in the greenhouse, plants were harvested for roots and shoot weight. Roots were washed and analyzed using the WhinRhizo software to determine total root surface area, as shown in FIG. 8. Strain 2 and the derivative populations tested in this study showed a positive trend of increased total root length in soybean when compared to untreated (i.e., water-treated) control ("UTC"). Further, derivatives G01 and C03 performed significantly (@ P 0.05) better than Strain 2 in increasing total root length.

Figure 9:
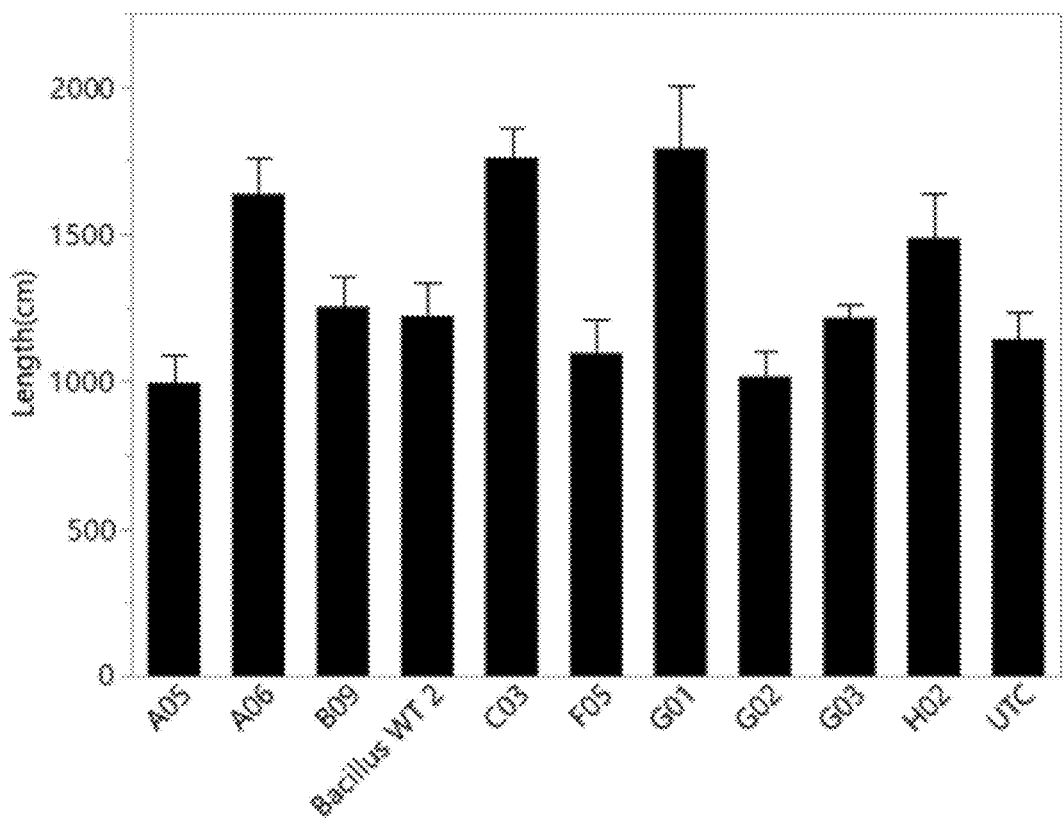
FIG. 9 shows total root length (in cm) obtained from two-week old soybean seedlings treated with Strain 2 (referred to in the figure as *Bacillus* WT 2) and selected derivative populations.

Root length from seed treated with Strain 2 and the various derivative populations is shown in FIG. 9. Strain 2 and most derivative populations tested in this study increased total root length in soybean when compared to UTC, and derivative G02, C03, A06 (@ P 0.05) performed significantly better than Strain 2 in increasing total root length. The number of roots with a diameter less than 0.5 mm, referred to as fine roots, was also measured for each replicate. Interestingly, certain derivative populations, A06, C03, G01 and H02 significantly increased the number of fine roots in comparison to Strain 2 and the water control (@ P=0.05).

Figure 10:
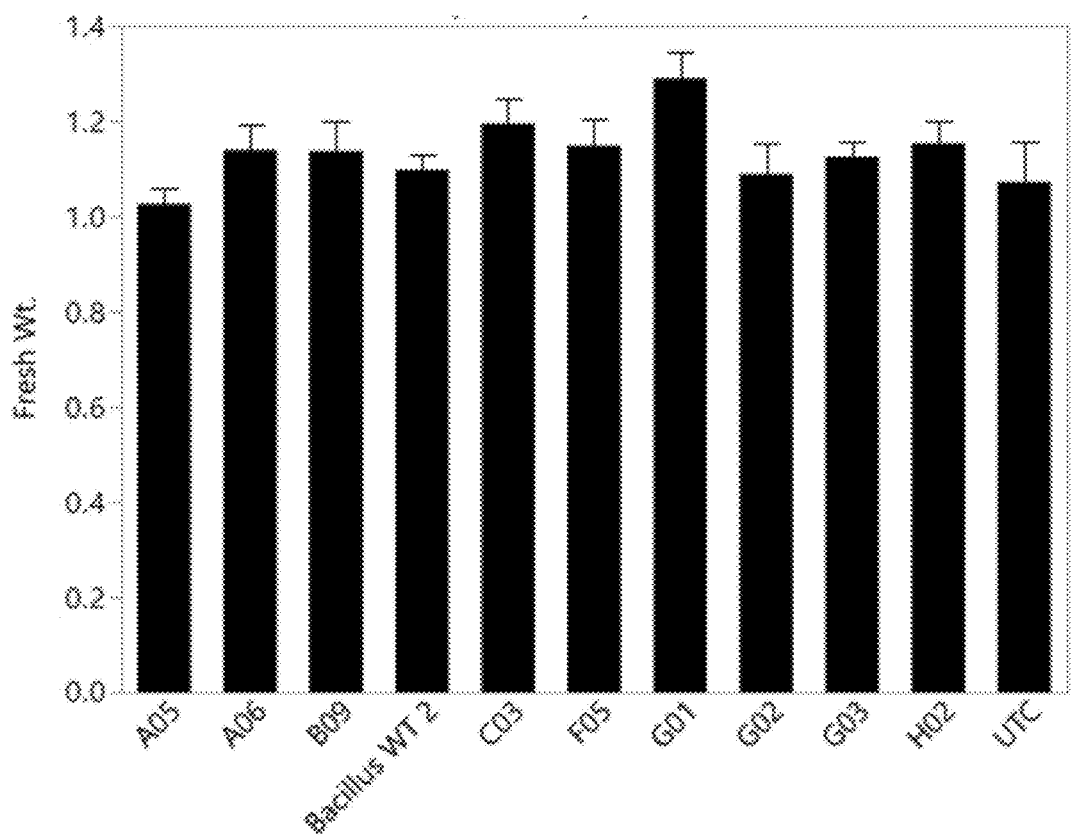
FIG. 10 shows total fresh shoot weight (in g) obtained from two-week old soybean seedlings treated with Strain 2 (referred to in the figure as *Bacillus* WT 2) and selected derivative populations.
Figure 11:
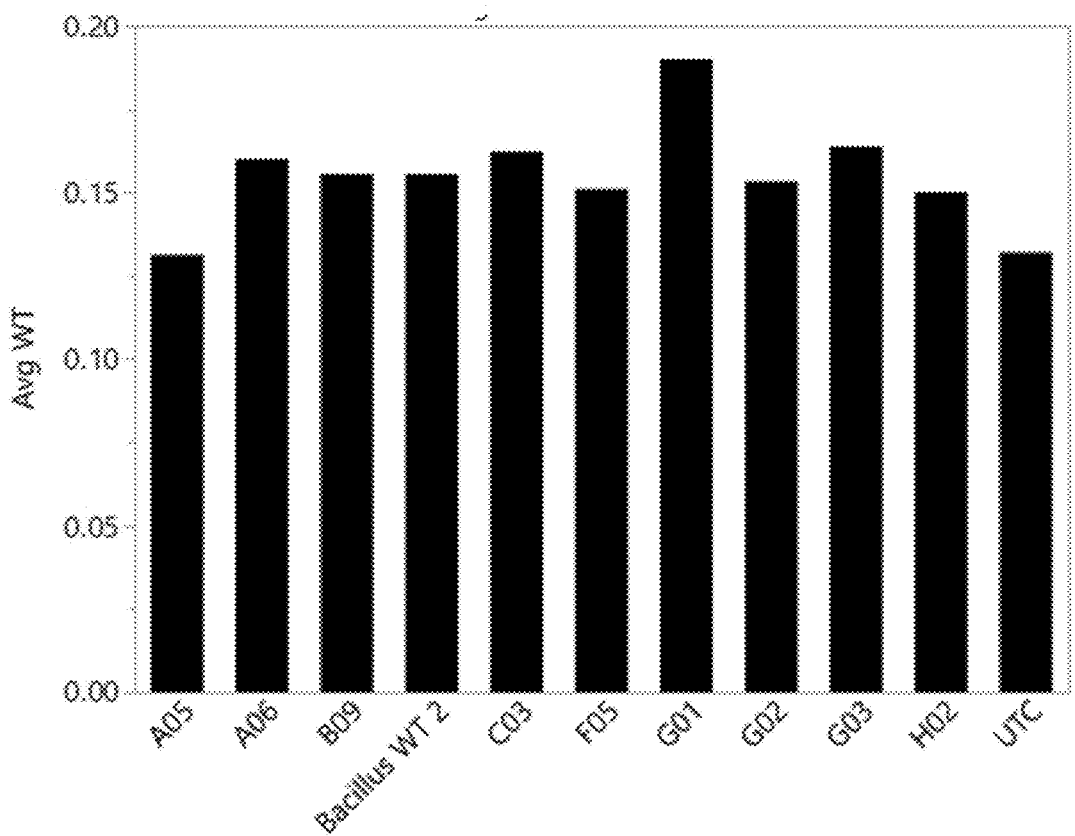
FIG. 11 shows total dry shoot weight (in g) obtained from two-week old soybean seedlings treated with Strain 2 (referred to in the figure as *Bacillus* WT 2) and selected derivative populations.

Total fresh shoot weight and total dry shoot weight from plants with seed treated with Strain 2 and its various derivative populations are shown in FIG. 10 and FIG. 11. Strain 2 and its derivative populations increased total shoot weight in soybean (when compared to UTC or water control), and some derivatives (G02, C03, H02) showed a trend of positive performance in increasing total shoot fresh weight in comparison to Strain 2. In addition, a selection of derivatives showed a positive trend of higher biomass accumulation as measured by dry weight when compared to Strain 2.

The invention claimed is:

1. A method for producing plant-associated soil microbial (PASM) cells, comprising:
   (a) growing a genetically uniform population of PASM cells in or on a first microbial growth medium comprising a plant root exudate compound;
   (b) harvesting at least some of the resulting PASM cells and growing the harvested PASM cells in or on a second microbial growth medium comprising the plant root exudate compound;
   (c) optionally repeating step (b) at least one time; and
   (d) selecting at least one PASM cell that is different compared to the genetically uniform population based on microbial traits.

2. The method of claim 1, wherein the PASM cells are grown to log phase during at least one of the growth phases required by steps (a) or (b).

3. The method of claim 1, wherein the plant root exudate compound is an antimicrobial compound that is antimicrobial with respect to the genetically uniform population of PASM cells grown in step (a).

4. The method of claim 1, wherein the plant root exudate compound is one or more of the following:
   (i) a phenol, a benzoxazinone, a flavonoid or isoflavonoid, a tannin, a coumarin, a terpenoid, an alkaloid, a t-cinnamic acid, a ferulic acid, a p-coumaric acid, a vanillic acid, a syringic acid, a 4-hydroxyphenylacetic acid, an indoleacetic acid, a benzoic acid, and a rosmarinic acid; and
   (ii) a plant-derived monosaccharide, amino acid, peptide, protein, carbohydrate, sugar alcohol and organic acid.

5. The method of claim 4, wherein the plant root exudate compound is an isoflavonoid selected from the group consisting of coumestrol, genistein, glycitein and daidzein.

6. The method of claim 1, wherein the at least one PASM cell is selected on the basis of one or more of the following microbial traits:
(i) an increased growth rate;
(ii) an increased cell length and/or cell size;
(iii) an increased biomass; and
(iv) enhanced ability to form biofilms
compared to the genetically uniform population of PASM cells grown in step (a).

7. The method of claim 1, wherein the at least one PASM cell is selected on the basis of one or more of the following:
(i) an increased resistance or novel immunity to the root exudate compound;
(ii) an increased resistance or novel immunity to the root exudate compound, wherein the root exudate compound is antimicrobial; and
(iii) an increased or novel ability to metabolize the root exudate compound;
compared to the genetically uniform population of PASM cells grown in step (a).

8. The method of claim 1, wherein the second microbial growth medium is a liquid medium and the at least one PASM cell is selected on the basis of the optical density of the PASM cells grown in the second microbial growth medium.

9. The method of claim 1, wherein the PASM cells are bacterial cells or fungal cells.

10. The method of claim 1, further comprising fermenting the selected at least one PASM cell.

11. The method of claim 1, further comprising applying the selected at least one PASM cell to a plant, a plant part or a locus surrounding the plant.

12. The method of claim 1, wherein the plant root exudate compound is from a soybean plant.

13. A method for producing PASM cells, comprising:
(i) growing a genetically uniform population of PASM cells in a chemostat in a microbial growth medium comprising a plant root exudate compound; and
(ii) selecting at least one PASM cell that is different compared to the genetically uniform population based on microbial traits.

14. The method of claim 13, wherein the plant root exudate compound is an antimicrobial compound that is antimicrobial with respect to the genetically uniform population of PASM cells grown in step (a).

15. The method of claim 13, wherein the plant root exudate compound is one or more of the following:
(i) a phenol, a benzoxazinone, a flavonoid or isoflavonoid, a tannin, a coumarin, a terpenoid, an alkaloid, a t-cinnamic acid, a ferulic acid, a p-coumaric acid, a vanillic acid, a syringic acid, a 4-hydroxyphenylacetic acid, an indoleacetic acid, a benzoic acid, and a rosmarinic acid; and
(ii) a plant-derived monosaccharide, amino acid, peptide, protein, carbohydrate, sugar alcohol and organic acid.

16. The method of claim 15, wherein the one or more plant root exudate compound is an isoflavonoid selected from the group consisting of coumestrol, genistein, glycitein and daidzein.

17. The method of claim 15, wherein the at least one PASM cell is selected on the basis of increased tolerance to the isoflavonoid.

18. The method of claim 13, further comprising sampling the PASM cells from an outflow of the chemostat to monitor genetic and/or phenotypic changes in the PASM cells.

19. The method of claim 13, wherein the concentration of the root exudate compound in the medium is increased during the growth of the PASM cells to increase selective pressure.

* * * * *